US012061286B2

(12) United States Patent
Rimini et al.

(10) Patent No.: US 12,061,286 B2
(45) Date of Patent: Aug. 13, 2024

(54) RADAR FOR DETECTING HUMAN BODY PART

(71) Applicant: QUALCOMM Incorporated, San Diego, CA (US)

(72) Inventors: Roberto Rimini, San Diego, CA (US); Arthur Gubeskys, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 181 days.

(21) Appl. No.: 16/808,282

(22) Filed: Mar. 3, 2020

(65) Prior Publication Data

US 2020/0297236 A1 Sep. 24, 2020

Related U.S. Application Data

(60) Provisional application No. 62/821,818, filed on Mar. 21, 2019.

(51) Int. Cl.
*A61B 5/05* (2021.01)
*G01S 7/02* (2006.01)
(Continued)

(52) U.S. Cl.
CPC ............... *G01S 7/415* (2013.01); *A61B 5/05* (2013.01); *G01S 7/023* (2013.01); *G01S 13/10* (2013.01);
(Continued)

(58) Field of Classification Search
CPC .......... G01S 7/415; G01S 7/023; G01S 13/10; G01S 13/88; G01S 7/02; A61B 5/05
(Continued)

(56) References Cited

U.S. PATENT DOCUMENTS 8,190,854 B2 5/2012 Codrescu et al.
8,755,738 B2 6/2014 Forutanpour et al.
(Continued)

FOREIGN PATENT DOCUMENTS

CN 101068123 A 11/2007
CN 102023292 A 4/2011
(Continued)

OTHER PUBLICATIONS

International Search Report and Written Opinion—PCT/US2020/023388—ISAEPO—dated Jul. 6, 2020.
(Continued)

*Primary Examiner* — Timothy A Brainard
*Assistant Examiner* — Ismaaeel A. Siddiquee
(74) *Attorney, Agent, or Firm* — Holland & Hart LLP

(57) ABSTRACT

Systems and methods for detecting a body part like a human hand near a base station or a user equipment are disclosed. A plurality of radar pulses is transmitted from a communication device in succession and the reflected plurality of radar pulses is received sampled and adaptively processed to remove transmit and receive antenna mutual coupling and clutter from stationary objects near the body part. In one aspect the adaptive processing is accomplished with a single tap adaptive filter. The processed signal may be used to determine if there is a human body part near the communication device allowing the device to determine whether it is safe for the device to transmit a millimeter wave communication signal.

30 Claims, 11 Drawing Sheets

(51) Int. Cl.
  *G01S 7/41* (2006.01)
  *G01S 13/10* (2006.01)
  *G01S 13/88* (2006.01)
  *A61B 5/0507* (2021.01)
  *A61B 5/11* (2006.01)

(52) U.S. Cl.
  CPC ............. *G01S 13/88* (2013.01); *A61B 5/0507* (2013.01); *A61B 5/1114* (2013.01); *A61B 2503/12* (2013.01); *A61B 2562/0257* (2013.01); *G01S 7/02* (2013.01)

(58) Field of Classification Search
  CPC . A61B 5/0507; A61B 5/1114; A61B 2503/12; A61B 2562/0257
  See application file for complete search history.

(56) References Cited

U.S. PATENT DOCUMENTS

| | | | |
|---|---|---|---|
| 9,369,187 B1* | 6/2016 | Sammeta | H04B 7/0802 |
| 10,135,294 B1* | 11/2018 | Leabman | H02J 50/80 |
| 10,871,549 B2 | 12/2020 | Rimini et al. | |
| 2006/0049992 A1 | 3/2006 | Tsai | |
| 2010/0245159 A1 | 9/2010 | Krikorian et al. | |
| 2011/0260920 A1 | 10/2011 | Dybdal et al. | |
| 2014/0098681 A1 | 4/2014 | Stager et al. | |
| 2014/0247757 A1* | 9/2014 | Rimini | H04B 1/525 370/278 |
| 2015/0078217 A1 | 3/2015 | Choi et al. | |
| 2015/0236413 A1 | 8/2015 | Turpin et al. | |
| 2016/0259037 A1* | 9/2016 | Molchanov | G01S 7/0233 |
| 2016/0341821 A1* | 11/2016 | Wang | B60L 53/126 |
| 2017/0290011 A1 | 10/2017 | Kushnir et al. | |
| 2018/0034156 A1* | 2/2018 | Zhang | H01Q 1/523 |
| 2018/0106897 A1* | 4/2018 | Shouldice | A61B 5/4818 |
| 2019/0238202 A1* | 8/2019 | Chavva | H04B 7/0617 |
| 2019/0353750 A1 | 11/2019 | Rimini et al. | |
| 2020/0259515 A1* | 8/2020 | Mueck | H04W 4/029 |
| 2021/0376664 A1* | 12/2021 | Park | H04W 52/283 |
| 2024/0073068 A1 | 2/2024 | Tu et al. | |

FOREIGN PATENT DOCUMENTS

| | | |
|---|---|---|
| CN | 102023292 B | 8/2012 |
| DE | 102015119482 A1 | 5/2017 |
| EP | 2352234 A1 | 8/2011 |
| EP | 3148051 A | 3/2017 |
| EP | 3511738 A2 | 7/2019 |

OTHER PUBLICATIONS

Lu G., et al: "Contact-free Measurement of Heartbeat Signal via a Doppler Radar using Adaptive Filtering", Image Analysis and Signal Processing (IASP), 2010 International Conference on, IEEE, Piscataway, NJ, USA, Apr. 9, 2010 (Apr. 9, 2010), pp. 89-92, XP031683479, 4 Pages, ISBN: 978-1-4244-5554-6, the whole document.

Mandal A., et al., "Digital Equalization for Cancellation of Noise-Like Interferences in Adaptive Spatial Filtering", Circuits, System and Signal Processing, Cambride, MS, US. vol. 36, No. 2, May 11, 2016, pp. 675-702, 28 Pages, XP036138834, Abstract Introduction.

* cited by examiner

RADAR FOR DETECTING HUMAN BODY PART

CLAIM OF PRIORITY UNDER 35 U.S.C. § 119

This application claims the benefit of U.S. Provisional Application Ser. No. 62/821,818 entitled "RADAR FOR DETECTING HUMAN BODY PART" filed on Mar. 21, 2019 which is expressly incorporated by reference herein in its entirety.

BACKGROUND

The following relates generally to wireless communication, and more specifically to radar in a millimeter wave communication device.

Wireless communications systems are widely deployed to provide various types of communication content such as voice, video, packet data, messaging, broadcast, and so on. These systems may support communication with multiple users by sharing the available system resources (e.g., time, frequency, and power). Examples of such multiple-access systems include code division multiple access (CDMA) systems, time division multiple access (TDMA) systems, frequency division multiple access (FDMA) systems, and orthogonal frequency division multiple access (OFDMA) systems, (e.g., Long Term Evolution (LTE) system, or a New Radio (NR) system). A wireless multiple-access communications system may include base stations (e.g., a gNB or eNB) or other access network nodes, each simultaneously supporting communication for multiple communication devices, which may be otherwise known as user equipment (UE).

In some wireless systems, base stations and UEs may communicate using directional millimeter wave transmissions (e.g., beams), where beamforming techniques may be applied using one or more antenna arrays to generate beams in different directions. Directional millimeter wave transmissions are expected to be utilized by many 5G compliant devices. Millimeter wave transmissions have a harmful effect on human skin. Accordingly, government regulating agencies often limit human tissue exposure to millimeter wave transmissions. For example, the Federal Communications Commission (FCC) has guidelines that indicate the Maximum Permissible Exposure (MPE) to millimeter wave energy averaged over 4 seconds is 1 mW/cm$^2$.

Because MPE limit is affected by the proximity of a user to a device's antenna, there is a need for systems and methods for communication devices that utilize millimeter wave radar to determine if there is a human body part in proximity to the device allowing the device to determine if a communication transmission may be made safely.

SUMMARY

In one or more aspects, a communication device transmits a plurality of millimeter wave radar pulses from one or more antenna elements. The communication device then receives the radar pulses reflected by the environment on one or more elements. The radar pulses are successively sampled on each of the received radar pulses in "fast time" and adaptively filtered along the slow time dimension to remove components of the received signals that are due to mutual coupling or clutter from static objects. The communication device can then determine if there is a human body part proximate to the communication device and if it is safe to transmit millimeter wave communication signals.

DETAILED DESCRIPTION

In one aspect, communication devices that transmit millimeter waves may feature a radar for determining if a body part is located near the communication device. The radar may be able to determine the range and direction to the body part allowing the communication device to determine if a millimeter wave communication transmission may be safely made from the device.

The communication device may transmit a plurality of millimeter wave pulses. The reflected pulses may then be received by the device and processed to remove any mutual coupling or clutter caused by static objects. In one exemplary aspect, an adaptive single tap low pass filter may be used to filter samples of the received millimeter wave pulses removing the mutual coupling and clutter received by the device. With the mutual coupling and clutter removed, reflections from a non-static object like a hand or other body part may be rendered apparent.

Figure 1:
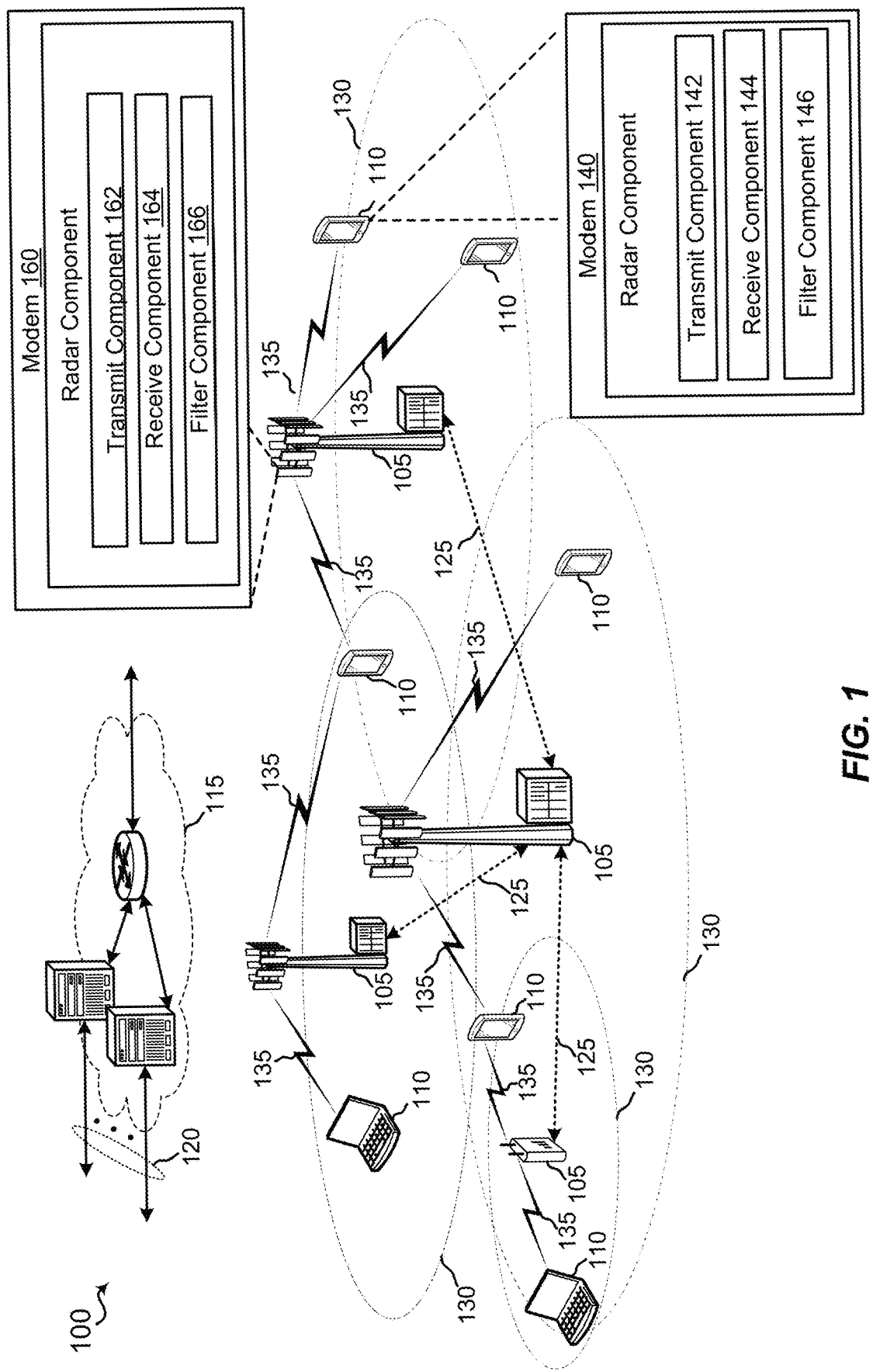
FIG. 1 illustrates an example of a system for wireless communication that supports radar detection and location of a human body part in accordance with aspects of the present disclosure.

FIG. 1 illustrates an example of a wireless communications system 100 in accordance with various aspects of the present disclosure. The wireless communications system 100 includes base stations 105, UEs 110, and a core network 115. In some examples, the wireless communications system 100 may be a Long-Term Evolution (LTE), LTE-Advanced (LTE-A) network, or a New Radio (NR) network. In some cases, wireless communications system 100 may support enhanced broadband communications, ultra-reliable (i.e., mission critical) communications, low latency communications, and communications with low-cost and low-complexity devices. Wireless communications system 100 may support the use of a difference in transmit and receive array gains for the calculation of an uplink transmit power. A power adjustment, duty cycle adjustment, or a no transmit decision may be made when millimeter wave transmissions are made near human beings.

Base stations 105 may wirelessly communicate with UEs 110 via one or more base station antennas. Each base station 105 may provide communication coverage for a respective geographic coverage area 130. Communication links 135 shown in wireless communications system 100 may include uplink transmissions from a UE 110 to a base station 105, or downlink transmissions, from a base station 105 to a UE 110. Control information and data may be multiplexed on an uplink channel or downlink according to various techniques. Control information and data may be multiplexed on a downlink channel, for example, using time division multiplexing (TDM) techniques, frequency division multiplexing (FDM) techniques, or hybrid TDM-FDM techniques. In some examples, the control information transmitted during a transmission time interval (TTI) of a downlink channel may be distributed between different control regions in a cascaded manner (e.g., between a common control region and one or more UE-specific control regions).

UEs 110 may be dispersed throughout the wireless communications system 100, and each UE 110 may be stationary or mobile. A UE 110 may also be referred to as a mobile station, a subscriber station, a mobile unit, a subscriber unit, a wireless unit, a remote unit, a mobile device, a wireless device, a wireless communications device, a remote device, a mobile subscriber station, an access terminal, a mobile terminal, a wireless terminal, a remote terminal, a handset, a user agent, a mobile client, a client, or some other suitable terminology. A UE 110 may also be a cellular phone, a personal digital assistant (PDA), a wireless modem, a wireless communication device, a handheld device, a tablet computer, a laptop computer, a cordless phone, a personal electronic device, a handheld device, a personal computer, a wireless local loop (WLL) station, an Internet of Things (IoT) device, an Internet of Everything (IoE) device, a machine type communication (MTC) device, an appliance, an automobile, or the like.

In some cases, a UE 110 may also be able to communicate directly with other UEs (e.g., using a peer-to-peer (P2P) or device-to-device (D2D) protocol). One or more of a group of UEs 110 utilizing D2D communications may be within the coverage area 130 of a cell. Other UEs 110 in such a group may be outside the coverage area 130 of a cell, or otherwise unable to receive transmissions from a base station 105. In some cases, groups of UEs 110 communicating via D2D communications may utilize a one-to-many (1:M) system in which each UE 110 transmits to every other UE 110 in the group. In some cases, a base station 105 facilitates the scheduling of resources for D2D communications. In other cases, D2D communications are carried out independent of a base station 105.

Some UEs 110, such as MTC or IoT devices, may be low cost or low complexity devices, and may provide for automated communication between machines, i.e., Machine-to-Machine (M2M) communication. M2M or MTC may refer to data communication technologies that allow devices to communicate with one another or a base station without human intervention. For example, M2M or MTC may refer to communications from devices that integrate sensors or meters to measure or capture information and relay that information to a central server or application program that can make use of the information or present the information to humans interacting with the program or application. Some UEs 110 may be designed to collect information or enable automated behavior of machines. Examples of applications for MTC devices include smart metering, inventory monitoring, water level monitoring, equipment monitoring, healthcare monitoring, wildlife monitoring, weather and geological event monitoring, fleet management and tracking, remote security sensing, physical access control, and transaction-based business charging.

In some cases, an MTC device may operate using half-duplex (one-way) communications at a reduced peak rate. MTC devices may also be configured to enter a power saving "deep sleep" mode when not engaging in active communications. In some cases, MTC or IoT devices may be designed to support mission critical functions and wireless communications system may be configured to provide ultra-reliable communications for these functions.

Base stations 105 may communicate with the core network 115 and with one another. For example, base stations 105 may interface with the core network 115 through backhaul links (e.g., S1, etc.). Base stations 105 may communicate with one another over backhaul links 134 (e.g., X2, etc.) either directly or indirectly (e.g., through core network 115). Backhaul links may be wired or unwired. Base stations 105 may perform radio configuration and scheduling for communication with UEs 110 or may operate under the control of a base station controller (not shown). In some examples, base stations 105 may be macro cells, small cells, hot spots, or the like. Base stations 105 may also be referred to as gNBs.

A base station 105 may be connected by an S1 interface to the core network 115. The core network may be an evolved packet core (EPC), which may include at least one mobility management entity (MME), at least one serving gateway (S-GW), and at least one Packet Data Network (PDN) gateway (P-GW). The MME may be the control node that processes the signaling between the UE 110 and the EPC. All user Internet Protocol (IP) packets may be transferred through the S-GW, which itself may be connected to the P-GW. The P-GW may provide IP address allocation as well as other functions. The P-GW may be connected to the network operators IP services. The operators IP services may include the Internet, the Intranet, an IP Multimedia Subsystem (IMS), and a Packet-Switched (PS) Streaming Service.

The core network 120 may provide user authentication, access authorization, tracking, Internet Protocol (IP) connectivity, and other access, routing, or mobility functions. At least some of the network devices, such as base station 105 may include subcomponents such as an access network entity, which may be an example of an access node controller (ANC). Each access network entity may communicate with a number of UEs 110 through a number of other access network transmission entities, each of which may be an example of a smart radio head, or a transmission/reception point (TRP). In some configurations, various functions of each access network entity or base station 105 may be distributed across various network devices (e.g., radio heads and access network controllers) or consolidated into a single network device (e.g., a base station 105).

Wireless communications system 100 may operate in an ultra-high frequency (UHF) frequency region using frequency bands from 700 MHz to 2600 MHz (2.6 GHz), although some networks (e.g., a wireless local area network (WLAN)) may use frequencies as high as 5 GHz. This region may also be known as the decimeter band, since the wavelengths range from approximately one decimeter to one meter in length. UHF waves may propagate mainly by line of sight, and may be blocked by buildings and environmental features. However, the waves may penetrate walls sufficiently to provide service to UEs 110 located indoors. Transmission of UHF waves is characterized by smaller antennas and shorter range (e.g., less than 100 km) compared to transmission using the smaller frequencies (and longer waves) of the high frequency (HF) or very high frequency (VHF) portion of the spectrum. In some cases, wireless communications system 100 may also utilize extremely high frequency (EHF) portions of the spectrum (e.g., from 30 GHz to 300 GHz). This region may also be known as the millimeter band, since the wavelengths range from approximately one millimeter to one centimeter in length. Thus, EHF antennas may be even smaller and more closely spaced than UHF antennas. In some cases, this may facilitate use of antenna arrays within a UE 110 (e.g., for directional beamforming). However, EHF transmissions may be subject to even greater atmospheric attenuation and shorter range than UHF transmissions.

Wireless communications system 100 may support mmW communications between UEs 110 and base stations 105 and in backhaul links. Devices operating in mmW or EHF bands may have multiple antennas to allow beamforming. That is, a base station 105 may use multiple antennas or antenna arrays to conduct beamforming operations for directional communications with a UE 110. Beamforming (which may also be referred to as spatial filtering or directional transmission) is a signal processing technique that may be used at a transmitter (e.g., a base station 105) to shape and/or steer an overall antenna beam in the direction of a target receiver (e.g., a UE 110). This may be achieved by combining elements in an antenna array in such a way that transmitted signals at particular angles experience constructive interference while others experience destructive interference.

Multiple-input multiple-output (MIMO) wireless systems use a transmission scheme between a transmitter (e.g., a base station 105) and a receiver (e.g., a UE 110), where both transmitter and receiver are equipped with multiple antennas. Some portions of wireless communications system 100 may use beamforming. For example, base station 105 may have an antenna array with a number of rows and columns of antenna ports that the base station 105 may use for beamforming in its communication with UE 110. Signals may be transmitted multiple times in different directions (e.g., each transmission may be beamformed differently). A mmW receiver (e.g., a UE 110) may try multiple beams (e.g., antenna subarrays) while receiving the synchronization signals.

In some cases, the antennas of a base station 105 or UE 110 may be located within one or more antenna arrays, which may support beamforming or MIMO operation. One or more base station antennas or antenna arrays may be collocated at an antenna assembly, such as an antenna tower. In some cases, antennas or antenna arrays associated with a base station 105 may be located in diverse geographic locations. A base station 105 may multiple use antennas or antenna arrays to conduct beamforming operations for directional communications with a UE 110.

In some cases, wireless communications system 100 may be a packet-based network that operate according to a layered protocol stack. In the user plane, communications at the bearer or Packet Data Convergence Protocol (PDCP) layer may be IP-based. A radio link control (RLC) layer may in some cases perform packet segmentation and reassembly to communicate over logical channels. A medium access control (MAC) layer may perform priority handling and multiplexing of logical channels into transport channels. The MAC layer may also use hybrid automatic repeat request (HARQ) to provide retransmission at the MAC layer to improve link efficiency. In the control plane, the radio resource control (RRC) protocol layer may provide establishment, configuration, and maintenance of an RRC connection between a UE 110 and a network device or core network 120 supporting radio bearers for user plane data. At the physical (PHY) layer, transport channels may be mapped to physical channels.

Wireless communications system 100 may support operation on multiple cells or carriers, a feature which may be referred to as carrier aggregation (CA) or multi-carrier operation. A carrier may also be referred to as a component carrier (CC), a layer, a channel, etc. The terms "carrier," "component carrier," "cell," and "channel" may be used interchangeably herein. A UE 110 may be configured with multiple downlink CCs and one or more uplink CCs for carrier aggregation. Carrier aggregation may be used with both FDD and TDD component carriers.

In some cases, wireless communications system 100 may utilize enhanced component carriers (eCCs). An eCC may be characterized by one or more features including: wider bandwidth, shorter symbol duration, shorter TTIs, and modified control channel configuration. In some cases, an eCC may be associated with a carrier aggregation configuration or a dual connectivity configuration (e.g., when multiple serving cells have a suboptimal or non-ideal backhaul link). An eCC may also be configured for use in unlicensed spectrum or shared spectrum (where more than one operator is allowed to use the spectrum). An eCC characterized by wide bandwidth may include one or more segments that may be utilized by UEs 110 that are not capable of monitoring the whole bandwidth or prefer to use a limited bandwidth (e.g., to conserve power).

In some cases, an eCC may utilize a different symbol duration than other CCs, which may include use of a reduced symbol duration as compared with symbol durations of the other CCs. A shorter symbol duration is associated with increased subcarrier spacing. A device, such as a UE 110 or base station 105, utilizing eCCs may transmit wideband signals (e.g., 20, 40, 60, 80 MHz, etc.) at reduced symbol durations (e.g., 16.67 microseconds). A TTI in eCC may consist of one or multiple symbols. In some cases, the TTI duration (that is, the number of symbols in a TTI) may be variable.

A shared radio frequency spectrum band may be utilized in an NR shared spectrum system. For example, an NR shared spectrum may utilize any combination of licensed, shared, and unlicensed spectrums, among others. The flexibility of eCC symbol duration and subcarrier spacing may allow for the use of eCC across multiple spectrums. In some examples, NR shared spectrum may increase spectrum utilization and spectral efficiency, specifically through dynamic vertical (e.g., across frequency) and horizontal (e.g., across time) sharing of resources.

In some cases, wireless communications system 100 may utilize both licensed and unlicensed radio frequency spectrum bands. For example, wireless communications system 100 may employ LTE License Assisted Access (LTE-LAA) or LTE Unlicensed (LTE U) radio access technology or NR technology in an unlicensed band such as the 5 Ghz Industrial, Scientific, and Medical (ISM) band. When operating in unlicensed radio frequency spectrum bands, wireless devices such as base stations 105 and UEs 110 may employ listen-before-talk (LBT) procedures to ensure the channel is clear before transmitting data. In some cases, operations in unlicensed bands may be based on a CA configuration in conjunction with CCs operating in a licensed band. Operations in unlicensed spectrum may include downlink transmissions, uplink transmissions, or both. Duplexing in unlicensed spectrum may be based on frequency division duplexing (FDD), time division duplexing (TDD) or a combination of both.

A UE 110 attempting to access a wireless network may perform an initial cell search by detecting a primary synchronization signal (PSS) from a base station 105. The PSS may enable synchronization of slot timing and may indicate a physical layer identity value. The UE 110 may then receive a secondary synchronization signal (SSS). The SSS may enable radio frame synchronization, and may provide a cell identity value, which may be combined with the physical layer identity value to identify the cell. The SSS may also enable detection of a duplexing mode and a cyclic prefix length. After receiving the PSS and SSS, the UE 110 may receive a master information block (MIB), which may be transmitted in a physical broadcast channel (PBCH) by the base station 105. The MIB may contain system bandwidth information, a system frame number (SFN), and a physical HARQ indicator channel (PHICH) configuration.

After decoding the MIB, the UE 110 may receive one or more system information blocks (SIBs). For example, SIB1 may contain cell access parameters and scheduling information for other SIBs. For instance, SIB1 access information, including cell identity information, and it may indicate whether a UE 110 is allowed to camp on a coverage area 130. SIB1 also includes cell selection information (or cell selection parameters) and scheduling information for other SIBs, such as SIB2. Decoding SIB1 may enable the UE 110 to receive SIB2, where SIB2 may contain radio resource control (RRC) configuration information related to random access channel (RACH) procedures, paging, physical uplink control channel (PUCCH), physical uplink shared channel (PUSCH), power control, sounding reference signal (SRS), and cell barring. Different SIBs may be defined according to the type of system information conveyed. In some cases, SIB2 may be scheduled dynamically according to information in SIB1, and includes access information and parameters related to common and shared channels.

After the UE 110 decodes SIB2, it may transmit a RACH preamble to a base station 105. For example, the RACH preamble may be randomly selected from a set of 64 predetermined sequences. This may enable the base station 105 to distinguish between multiple UEs 110 trying to access the system simultaneously. The base station 105 may respond with a random access response that provides an uplink resource grant, a timing advance, and a temporary cell radio network temporary identifier (C-RNTI). The UE 110 may then transmit an RRC connection request along with a temporary mobile subscriber identity (TMSI) (e.g., if the UE 110 has previously been connected to the same wireless network) or a random identifier. The RRC connection request may also indicate the reason the UE 110 is connecting to the network (e.g., emergency, signaling, data exchange, etc.). The base station 105 may respond to the connection request with a contention resolution message addressed to the UE 110, which may provide a new C-RNTI. If the UE 110 receives a contention resolution message with the correct identification, it may proceed with RRC setup. If the UE 110 does not receive a contention resolution message (e.g., if there is a conflict with another UE 110), the UE 110 may repeat the RACH process by transmitting a new RACH preamble.

Wireless devices in wireless communications system 100 may send transmissions in accordance with a certain link budget. The link budget may account for allowed signal attenuation between a UE 110 and a base station 105, as well as antenna gains at the UE 110 and base station 105. Accordingly, the link budget may provide, for example, a maximum transmit power for the various wireless devices within wireless communications system 100. In some cases, a UE 110 may coordinate transmit power with a serving base station 105 to mitigate interference, improve the uplink data rate, and prolong battery life. FIG. 1 illustrates an example of a system for wireless communication that supports beam recovery in accordance with aspects of the present disclosure.

Some of the communication devices in wireless communication system 100 may have modems that include a radar component. For example, a base station 105 may have a base station modem 160 having a radar component. The radar component may have a transmit component 162 for transmitting one or more radar pulses. The radar component may also have a receive component 164 for receiving one or more radar pulses. The radar component may also have a filter component 166 for filtering the radar pulses. The filter component may be adapted to sample and adaptively filter the received pulses to remove clutter originated from static objects or mutual coupling originated from transmit and receive antenna arrays. The radar component may allow the base station to determine if there is a human hand or other body part proximate to the base station 105 informing the base station if it is safe to transmit a millimeter wave communication signal.

A UE 110 may have a UE modem 140 featuring a radar component. The radar component may have a transmit component 142 for transmitting one or more radar pulses. The radar component may also have a receive component 144 for receiving one or more radar pulses. The radar component may also have a filter component 146 for filtering the radar pulses. The filter component may be adapted to adaptively filter the received pulses to remove clutter from static objects or mutual coupling from transmit and receive antenna arrays. The radar component may allow the UE 110 to determine if there is a human hand or other body part proximate to the base station informing the UE if it is safe to transmit a millimeter wave communication signal.

Figure 2:
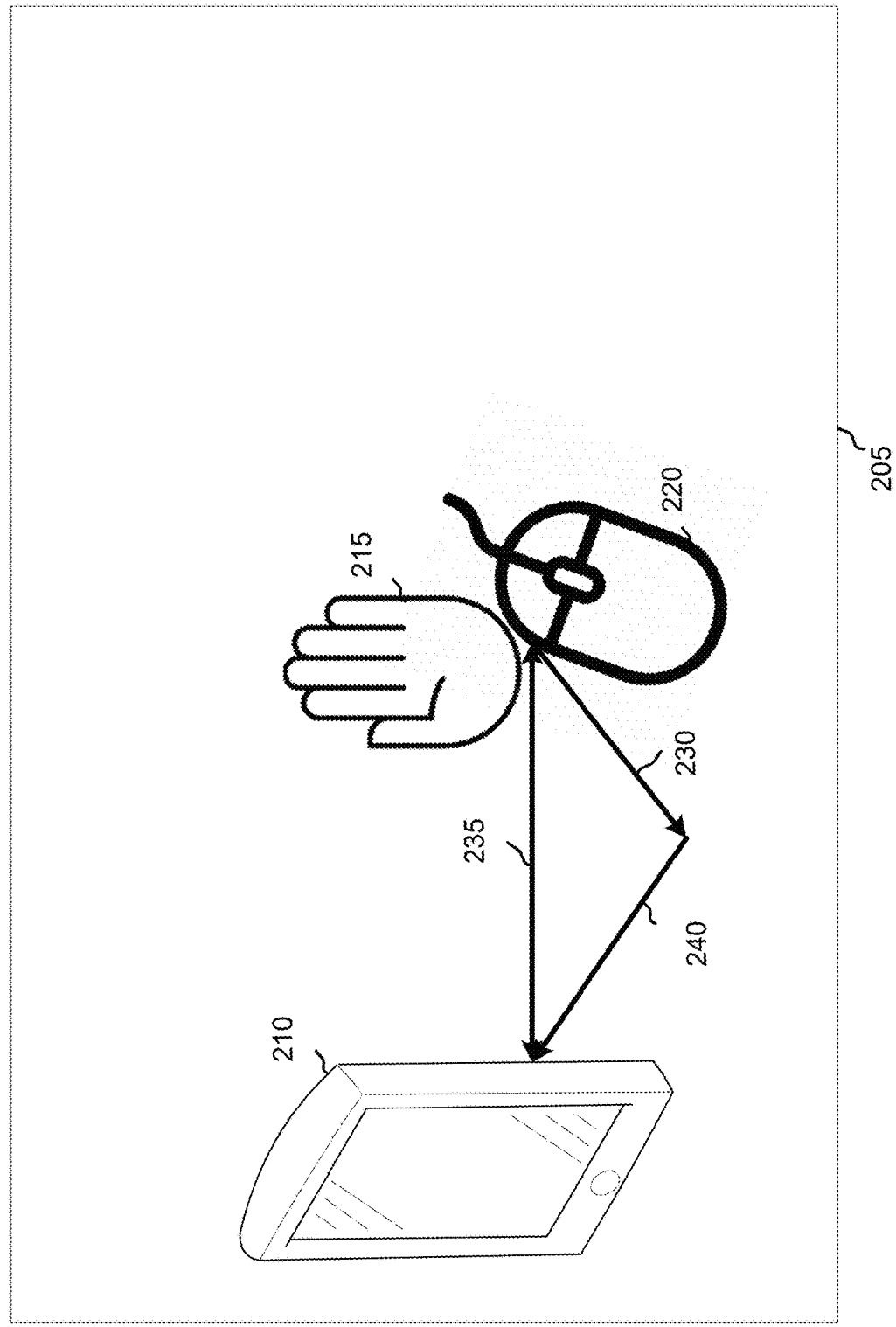
FIG. 2 illustrates an example of a communication device transmitting and receiving a plurality of radar pulses in accordance with aspects of the present disclosure.

FIG. 2 illustrates an example of a communication device transmitting and receiving a plurality of radar pulses 200 in accordance with aspects of the present disclosure. Shown in FIG. 2 are a tabletop 205, a UE 210, a human hand 215 and a mouse 220. The UE 210 has a radar for determining if a human body part is present. Notably, the human hand 215 has dynamics in that the human hand 215 moves frequently by nature of nerves responses. The mouse 220 and the tabletop 205 in contrast are static objects and stationary unless the human hand 215 interacts with them.

To determine if there is a human body part proximate to the UE 210, the UE may transmit a plurality of radar pulses 235. The plurality of pulses 235 are reflected by the human hand 215 and the mouse 220. The reflected energy from the plurality of pulses may then be received by UE 210. Some energy from the plurality of pulses 235 will be reflected directly back to the UE 210 while some of the energy may be reflected indirectly 230, 240 to the UE 210 bouncing off objects such as the table 205.

Reflected energy from static objects such as the mouse 220 will appear as clutter in the plurality of pulses received at the UE 210. In various aspects, the received radar pulses may be successively sampled at the same time in fast time (the time from the beginning of each pulse). A low pass filter may then be used to generate a clutter cancellation signal. The clutter cancellation signal may then be subtracted from the received signal samples to remove the clutter. After removing the clutter, the UE 210 may process the signals to determine the range and direction to a dynamic object such as a human hand and to determine if it is safe to transmit a millimeter wave communication signal.

Figure 3:
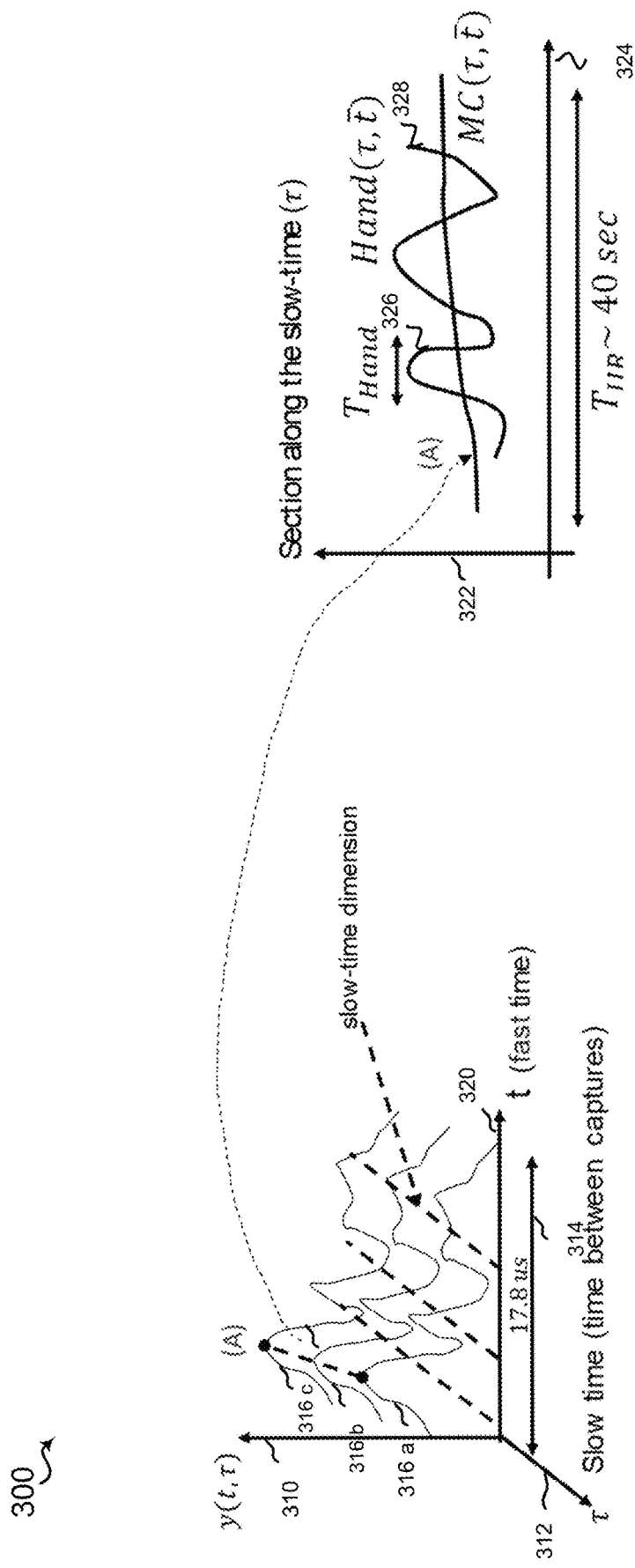
FIG. 3 illustrates an example of a plurality of radar pulses received at a communication device in accordance with aspects of the present disclosure.

FIG. 3 illustrates an example of a plurality of radar pulses received at a communication device in accordance with aspects of the present disclosure. Shown in FIG. 3 is a three dimensional axis, with y(t,τ) 310 shown on the vertical axis, t 320 (fast time) shown on the horizontal axis 320, and τ 312 (slow time) show on the axis coming out of the paper. A receive first radar plus 316a, a received second radar pulse 316b and a received third radar pulse 316c are also shown. Successive radar pulses are omitted for simplicity. Section line (A) along the slow-time axis τ 312 is projected on a second axis. The second axis has a vertical axis y(τ) 322 and a horizontal axis t 324 (fast time). The energy level of the hand 326 is shown as well as energy level of mutual coupling 328 MC (τ,t) between a transmit and receive antenna.

In millimeter wave transmissions a small distance between the radiating and receiving antenna may result in a large amount of transmitted energy leaking from the transmit antenna to the receive antenna. This mutual coupling may result in an energy level of mutual coupling 326 that may even be several orders of magnitude greater than the received energy level of a hand 328. To determine if a hand or other body part is present in the received radar pulses 316, it is desirable to remove the energy level of the mutual coupling 328 from the received radar pulses.

Mutual Coupling cannot be characterized completely by factory level measurements because the characteristics may change slowly over time due to temperature, load variations or for other reasons. Thus, the energy level of the mutual coupling 328 may vary slowly over time. In contrast, the energy level of a hand 326 or other body part will vary more quickly in time.

Accordingly, in many aspects of the invention a low pass filter may be used to characterize the energy level of the mutual coupling 328 so that it may be removed allowing the communication device to determine if a hand or other body part is present. In one exemplary embodiment, an Infinite Impulse Response (IIR) low pass filter with a sufficiently long time constant may be used to characterize the energy level of the mutual coupling 328 and cancel it from the signal.

It can be appreciated that the communication device in addition to sampling along Section A along the slow time line, the communication device may sample many Sections over fast time corresponding to different ranges of reflected radar pulses. Each of the section samples may be use by the communication device to determine the range to the hand or body part.

Figure 4:
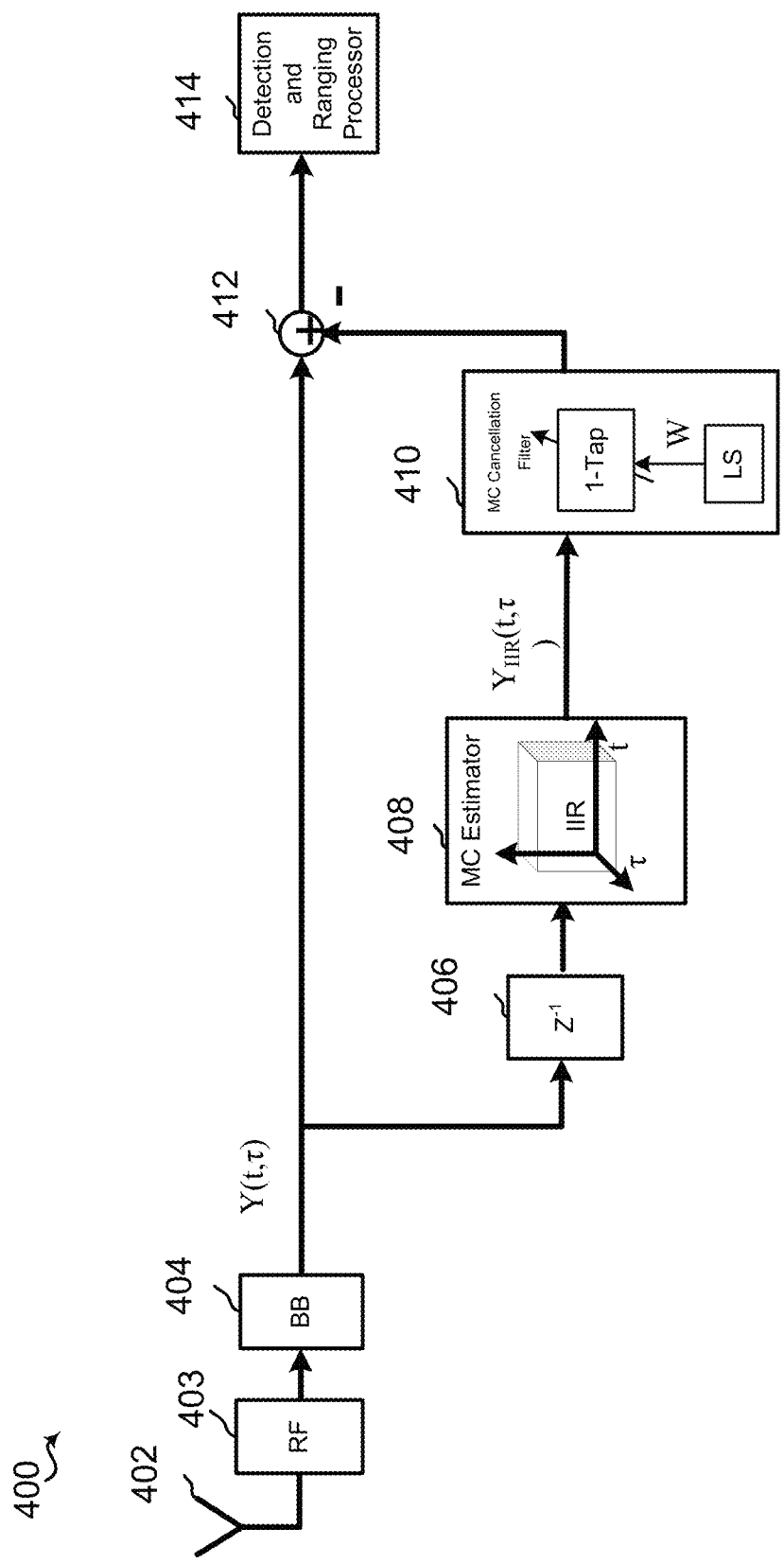
FIG. 4 illustrates an example of a communication device processing a plurality of radar pulses in accordance with aspects of the present disclosure.

FIG. 4 illustrates an example of a communication device processing a plurality of radar pulses in accordance with aspects of the present disclosure. The processing may be used to characterize and remove the mutual coupling component of transmit and receive antennas as well as the clutter component from static objects.

FIG. 4 shows an antenna 402 coupled with an RF front end 403 coupled with a base band processor. Also shown is a zero order hold 406, a Mutual Clutter (MC) Estimator 408 and an MC cancellation filter 410. A summer 412 and a detection and ranging processor 414 are also depicted.

Radar pulses may be received at antenna 402 and flow through the RF front end 403 to the baseband processor 404 producing y(t,τ). To characterize the mutual coupling component and the clutter component a zero order hold 406 is applied to Y(t,τ) and fed to mutual coupling estimator 408 having an infinite impulse response filter that produces output $Y_{IIR}(t,\tau)$. $Y_{IIR}(t,\tau)$ is processed by MC Cancellation Filter 410 having a single tap with a least squares weight W. The output of the MC Cancellation filter is then fed into a summer 412 where it is subtracted from Y(t,τ). The output of the summer is then processed by the detection and ranging processor 414 to determine if there is a hand or body part proximate the communication device.

Those skilled in the art will recognize that other aspects may include MC estimators with FIR filters or other known filters. MC cancellation filters may include other types of adaptive filters.

Figure 5:
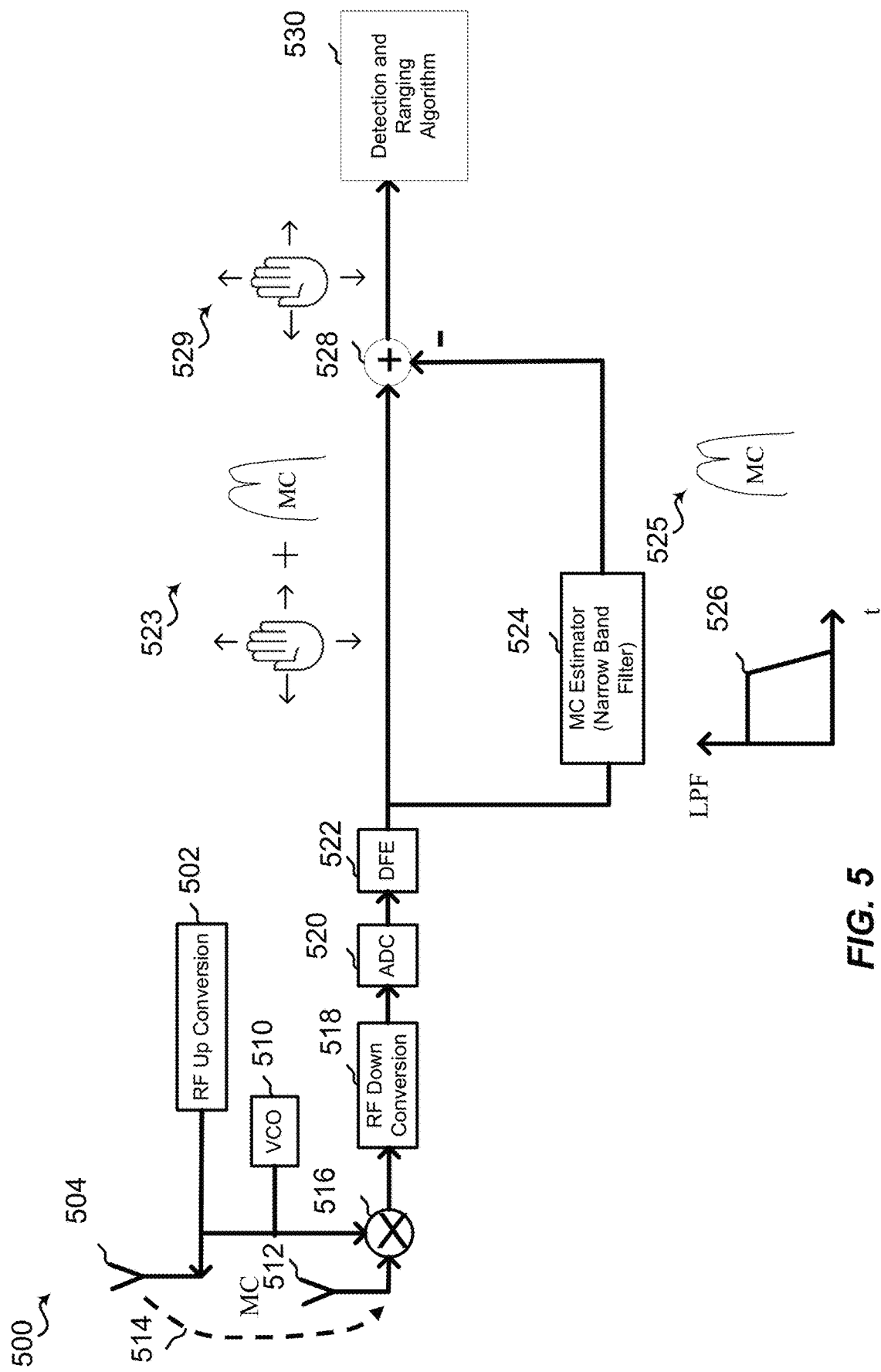
FIG. 5 illustrates an example of the communication device processing a plurality of radar pulses when a human body part is present in accordance with aspects of the present disclosure.

FIG. 5 illustrates an example of the communication device processing a plurality of radar pulses when a human body part is present in accordance with aspects of the present disclosure. Shown in FIG. 5 is an RF up converter 502 connected with a transmit antenna 504 and voltage-controlled oscillator 510. Also shown is a receive antenna 512 that is mutually coupled 514 with the transmit antenna 504. A mixer 516 is shown to represent the mixing of the receive antenna signals and mutual coupling (Tx-RX leakage). The output of the mixer 516 is connected with an RF down converter 518 that in turn is coupled with an analog to digital converter 520 that feeds a digital front end 522. The digital front end 522 is coupled with a mutual coupling estimator 524 having a low pass frequency response 526. A summer 528 is connected with the mutual coupling estimator 524 and the digital front end 522. The output of the summer 528 is connected with a detection and ranging processor 530.

A plurality of radar pulses may be upconverted in the RF up converter 502. The radar pulses may be transmitted through transmit antenna 504. The plurality of radar pulses may then be received by receive antenna 512 where they will be mixed with a mutual coupling component. The plurality of radar pulses may then be down converted in RF down converter 518 and digitized in analog to digital converter 520. The down converted and digitized signal be processed by the digital front end 522 producing a first signal that represents a hand plus mutual coupling 523. The signal may be filtered to extract the mutual component using the mutual coupling estimator 524. The extraction of mutual coupling from the composite observed signal is made possible by virtue of the slow changing nature of the mutual coupling with respect to inherent movements of humans. The low pass filter, which applies a low pass filtering along the slow time direction, retains the mutual coupling component while filtering out the fast changing component associated to human movements, thus producing a second signal that represents the mutual clutter 525. The second signal may be subtracted from the first signal in summer 528 leaving a third signal that represents the hand 529. The hand signal may be processed by the detection and ranging processor 530 determining that a hand is present and the range to the hand.

Figure 6:
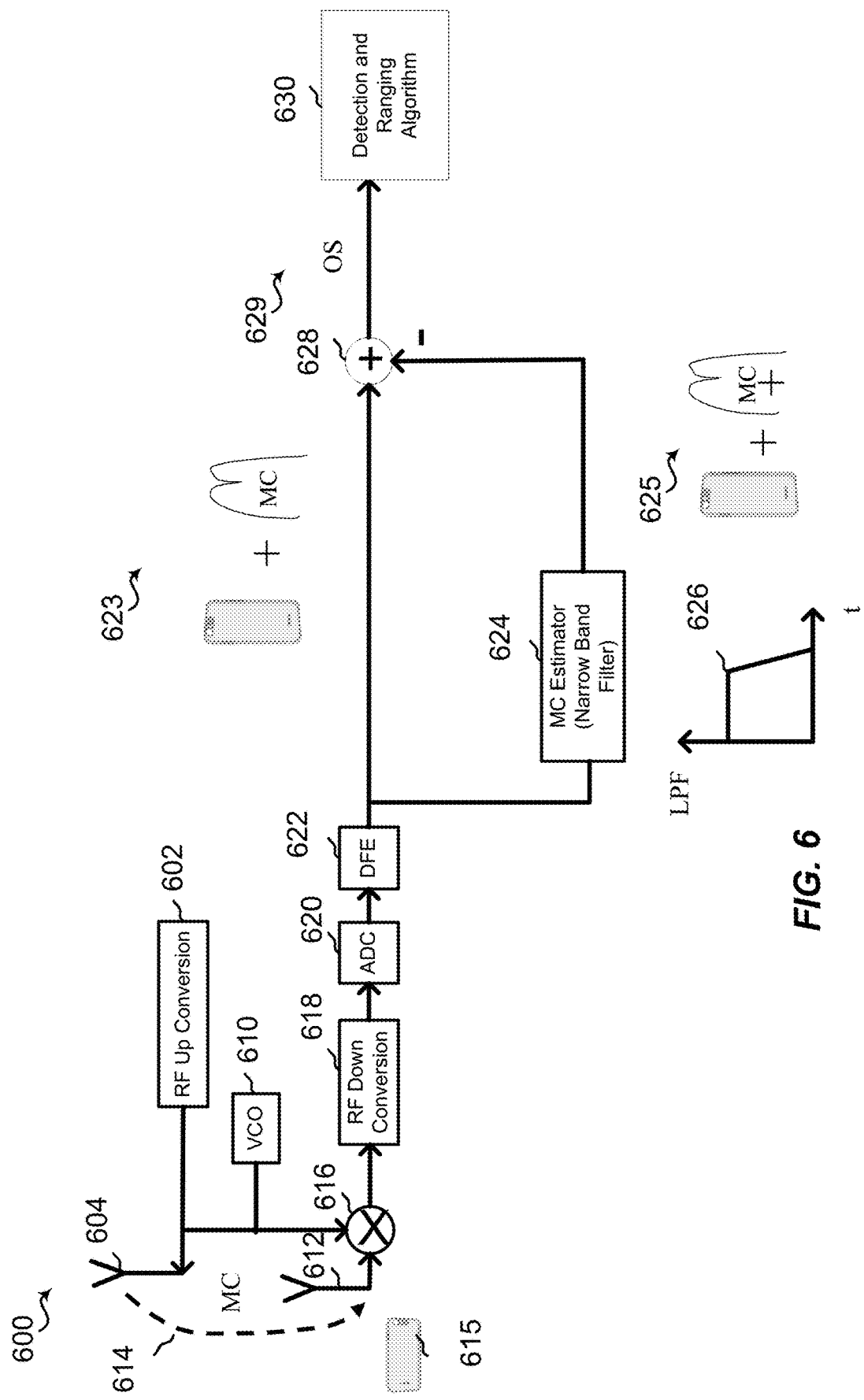
FIG. 6 illustrates an example of the communication device processing a plurality of radar pulses when a human body part is not present but a phone with a cover is in accordance with aspects of the present disclosure.

FIG. 6 illustrates an example of the communication device processing a plurality of radar pulses when a human body part is present but a phone with a cover is in accordance with aspects of the present disclosure. Shown in FIG. 6 is an RF up converter 602 connected with a transmit antenna 604 and voltage-controlled oscillator 610. Also shown is a receive antenna 612 that is mutually coupled 614 with the transmit antenna 604. A mixer 616 is shown to represent the mixing of the receive antenna signals, mutual coupling (Tx-RX leakage) and perturbation from the phone cover. The output of the mixer 616 is connected with an RF down converter 618 that in turn is coupled with an analog to digital converter 620 that feeds a digital front end 622. The digital front end 622 is coupled with a mutual clutter estimator 624 having a low pass frequency response 626. A summer 628 is connected with the mutual clutter estimator 624 and the digital front end 622. The output of the summer 628 is connected with a detection and ranging processor 630.

A plurality of radar pulses may be upconverted in the RF up converter 602. The radar pulses may be transmitted through transmit antenna 604. The plurality of radar pulses may then be received by receive antenna 612 where they will be mixed with a mutual coupling component and a perturbation from the phone cover. The plurality of radar pulses may then be down converted in RF down converter 618 and digitized in analog to digital converter 620. The down converted and digitized signal be processed by the digital front end 622 producing a first signal that represents mutual clutter plus the phone cover perturbation 623. The signal may be filtered using the mutual clutter estimator 624 as described earlier producing a second signal that represents the mutual clutter plus the phone cover perturbation 625. The second signal may be subtracted from the first signal in summer 628 leaving an output signal 629 with neither the mutual clutter or the phone cover perturbation. The output signal 629 may be processed by the detection and ranging processor 630 determining that a hand is not present or body part is not present.

Figure 7:
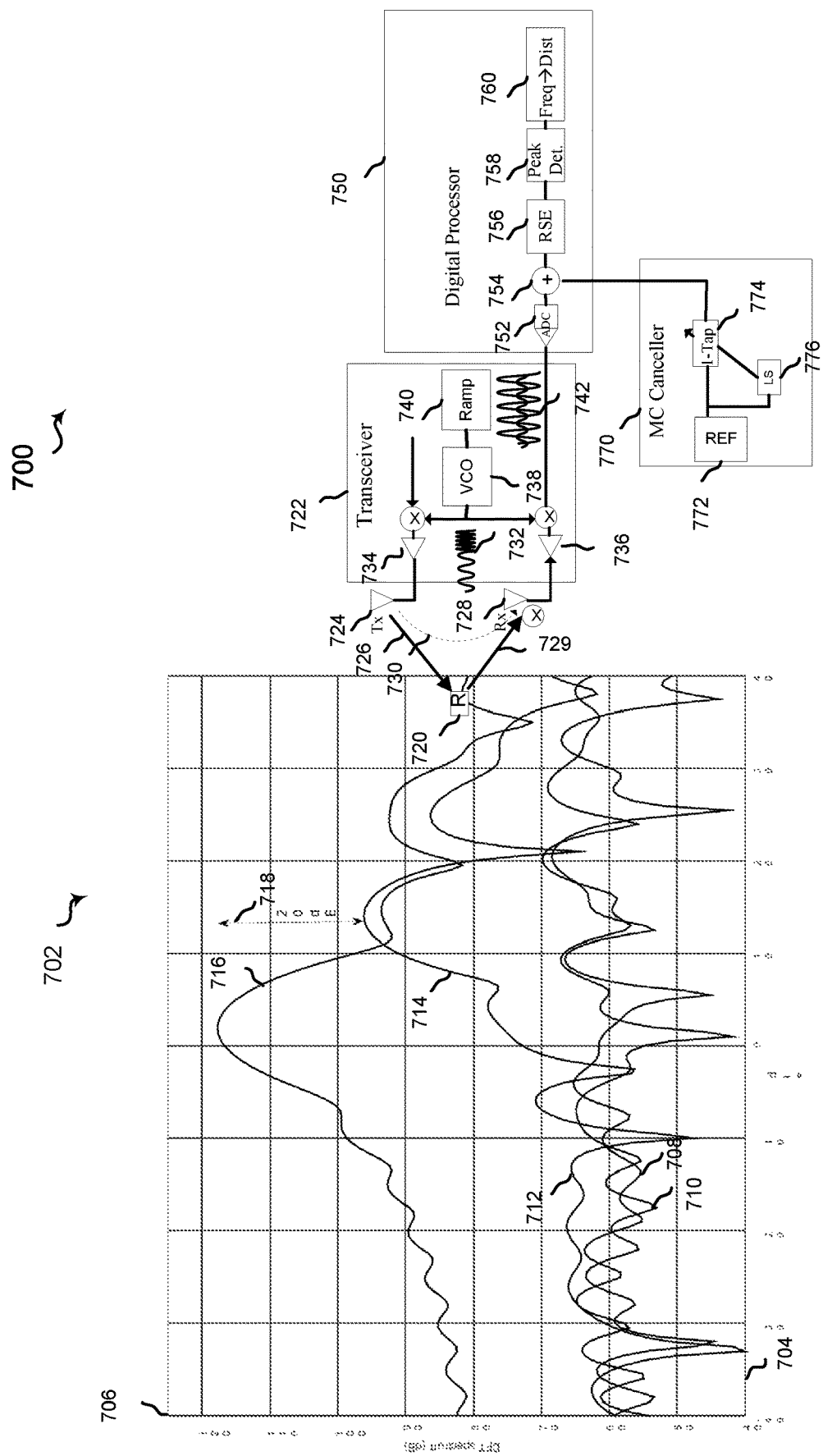
FIG. 7 illustrates an example of the communication device processing signals to cancel mutual coupling and transmit to receiver leakage.

FIG. 7 illustrates an example of the communication device processing signals 700 to cancel mutual coupling and/or cancel transmit to receiver leakage. An example DFT spectral plot 702 across different realizations and distances for a communication device using a FMCW radar is shown. Along the abscissa 704 the distance from a reflector (or target) is shown. Along the ordinate axis 706 the DFT spectrum is shown. A first noise signal 708 and a second noise signal 710 are shown on the spectral plot 702. Also shown are shown are preprocessed signal 716 and post mutual coupling processed signal 714. In this example, at 13 cm there is about a 20 dB difference 718 between the preprocessed signal 716 and the processed signal 714.

The DFT spectral plot 702 may have been generated using the received signals 720 from a transceiver 722 having a transmit antenna capable of transmitting radar signal 726. The transceiver 722 may have a receive antenna 728 capable of receiving reflected radar signals. Mutual coupling 730 noise from transmit antenna 724 to receive antenna 728 is also shown Transmitter receiver leakage 732 from the transceiver 722 is also apparent. The transceiver 722 has a power amplifier 734, a low noise amplifier 736, a voltage control oscillator 738, and a ramp function generator 740. An analog beating signal 742 is also shown.

A digital processor 750 connected with transceiver 722 has an analog to digital converter 752 connected with summer 754. The output of the summer 754 is connected with a range spectrum estimator 756. The range spectrum estimator 756 output is connected with a peak detector 758. The peak detector 758 in turn is connected to the frequency distance estimator 760.

A mission clutter canceller 770 is also shown. The mission clutter canceller 770 has a mission clutter reference signal generator 772. A least squares estimator 774 is connected to a one tap adaptive filter 774. The output of the mission clutter canceler is connected to the summer 754 in the digital processor 750.

Referring to Figure to FIG. 7 those skilled in the art will recognize that detection of FMCW radar signals at close range has some challenges. Mutual coupling 730 may be 20 dB or greater than the received radar signals 729 at short ranges. It is also difficult to characterize mutual coupling a priori since mutual coupling is a function of temperature and environment. The use of a mutual coupling filter, such as the shown mutual coupling filter 770, may be used to cancel the mutual coupling energy allowing the communication device to detect an further process received radar signals 729.

In the DFT spectral plot the first noise signal 708 and 710 signal may be a result of mutual coupling and\or transceiver 750 leakage. The superposition of noise signals may make it difficult to detect a preprocessed radar signal such as preprocessed radar signal 716. However, radar signal 716 may be processed using the mission clutter cancelling filter shown in FIG. 7. After processing, it may be possible to improve the radar signal to mutual coupling noise ratio and allow detection of reflected radar signals. In this example, a 20 dB 718 improvement is shown at 13 cm.

A communication device having a transceiver such as transceiver 722 may be used to transmit radar signals 726. A ramp generator 740 may be used to generate a ramp signal that drives a voltage control oscillator 738. The voltage control oscillator output may be mixed with a pulse and amplified by amplifier 734 to generate radar pulses. The radar pulses may be transmitted from a transmit antenna 724 and reflected back from a target. The received radar signals may be combined with an unwanted mutual coupling 730 noise signal before being amplified by low noise amplifier 736 and generating the an analog beating signal 742. The beating signal may be then processed by a digital processor 750.

The mutual clutter canceller 770 may generate adaptively a signal that may be summed with the beating signal to cancel the mutual coupling portion of the beating signal. In this example a reference signal 772 similar in character to the communications devices mutual clutter noise may be used by a single tap 774 least squares 776 adaptive filter to generate a mission clutter canceller output signal. The adaptive nature of the mutual clutter canceller 770 may adjust to the slowly varying character of the mutual coupling which may change as temperature and environment change.

The digital processor 750 may digitize the analog beating signal 742 using ADC 752 and may sum the newly generated digitized beating signal with the output of the mission clutter canceller 770 with summer 754 canceling the mutual coupling component of the received signal. With the mutual coupling noise removed or vitiated, the digital processor may in turn perform range spectrum estimation and peak detection.

Figure 8:
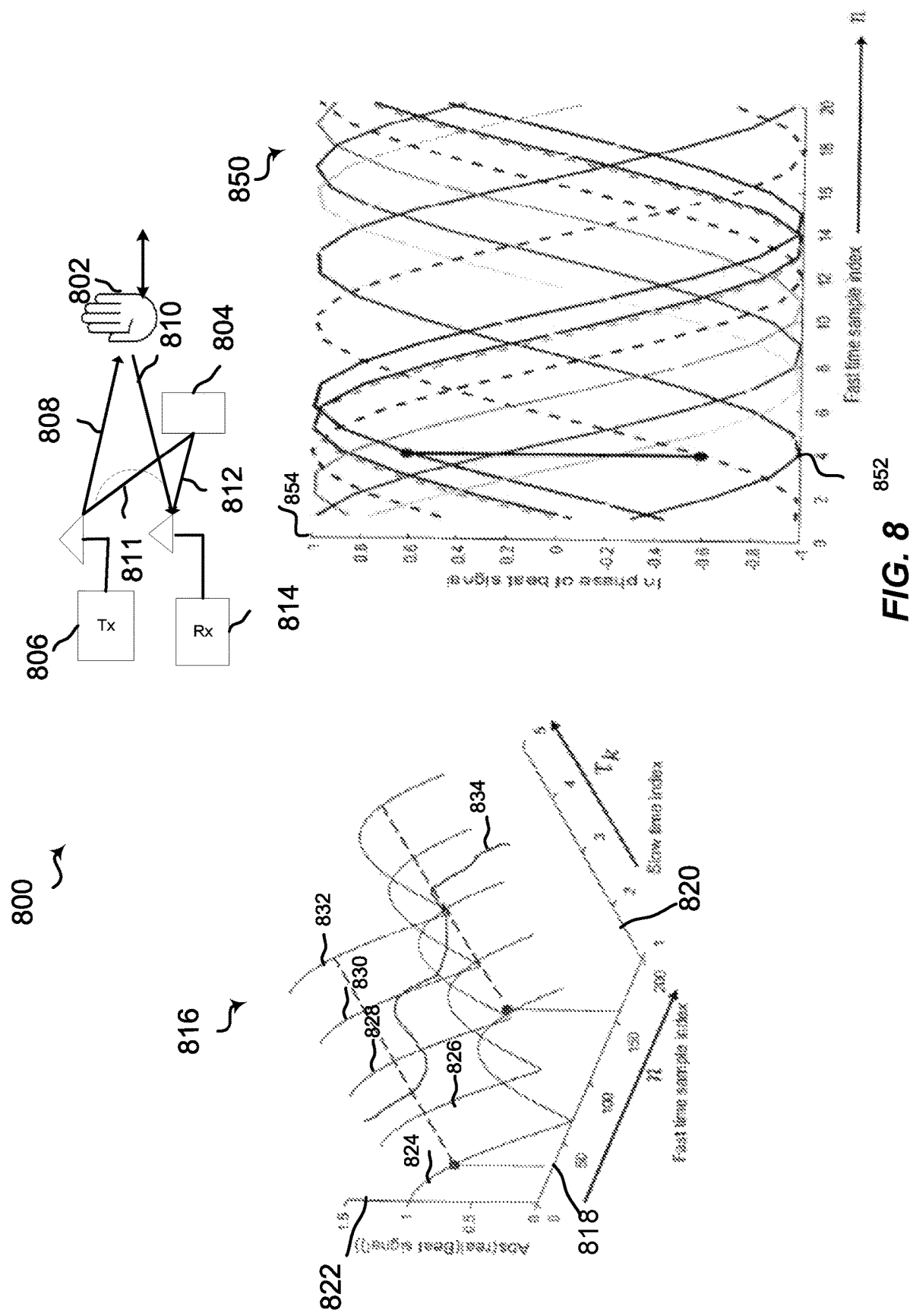
FIG. 8 illustrates an example of how the communication device may adaptively estimate mutual coupling.

FIG. 8 illustrates an example of how the communication device may adaptively estimate mutual coupling 800. Shown in FIG. 8 is a moving body part such as a hand 802 and a static target such as static target 804. A transmitter 806 capable of transmitting a plurality of radar pulses 808 is also shown along with a plurality of hand reflected radar pulses 810 and static target reflected radar pulses 812. The hand reflected radar pulses 810 and the target reflected radar pulses are reflected to a receiver 814.

Also shown in FIG. 8 is a first plot 816. A fast time axis 818 shows time in μS and a slow time index shows successive radar pulses τ 820. The first plot 816 also has an ordinate axis showing the absolute reflected pulse energy at receiver 814. The first plot shows a first reflected pulse 824, a second reflected pulse 826, a third reflected pulse 828, a fourth reflected 830 and a fifth reflected pulse 832. A beat signal 834 that varies from pulse to pulse over time is also shown.

A second plot 850 is also shown in FIG. 8 shows beat signals overlaid across successive pulses in slow time. The abscissa 852 of the second plot 850 shows the fast time sample index (n) and the ordinate 854 of the second plot shows the phase of the overlaid beat signals.

Those skilled in the art will recognize that the moving hand 802 will produce a random phase shift in the in the reflected pulse energy over time. A change in distance Δd of the moving hand 802 may change the phase by 4ΠΔd/λ whereas the static target 804 will not produce a random phase shift. The moving hand 802 will thus produce random like phase shifts in the hand reflected radar pulses 810 unlike the static target 804 in which there will be no apparent random phase shifts in the static target reflected radar pulses. Thus a low pass filter such as the filter shown in FIG. 7 may be used to extract the static component of the received signal samples while filtering out dynamic targets such as the moving hand 802. Mutual coupling 811 with its very slow changing characteristics will also appear as a slowly varying target. Thus, the low pass filter may be used to generate a cancellation signal for removing both mutual coupling and static targets like the low pass filter shown in FIG. 7.

Figure 9:
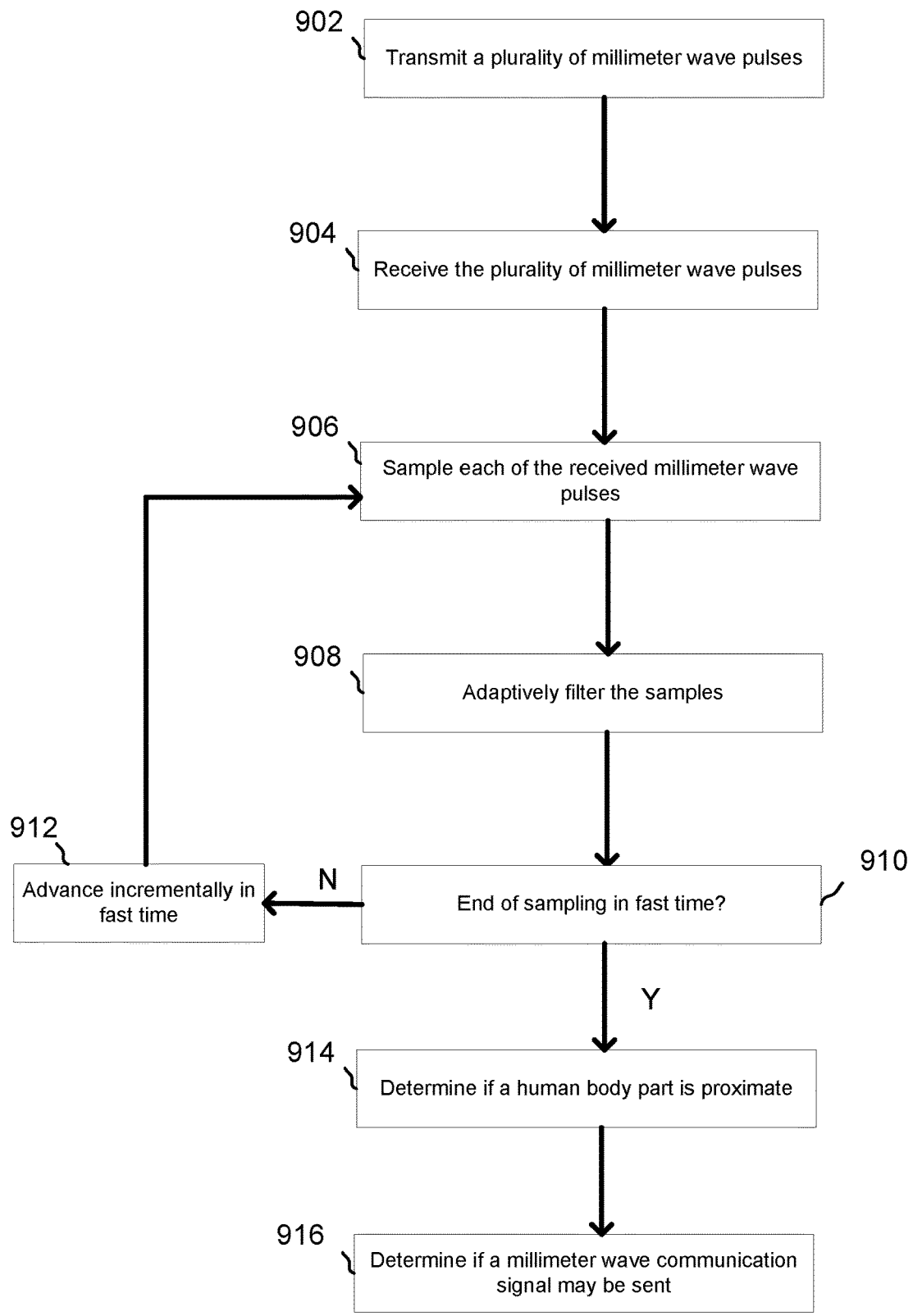
FIG. 9 is an exemplary flow diagram of a communication device radar pulses in accordance with aspects of the present disclosure.

FIG. 9 is an exemplary flow diagram of a communication device radar pulses in accordance with aspects of the present disclosure. The communication device may transmit a plurality of millimeter wave pulses 902. The pulse duration occurring in fast time and the time between pulses occurring in slow time. Those skilled in the art will recognize that radar pulses may be transmitted at a Pulse Repetition Interval (PRI) with fast time representing the time duration of each pulse transmission. Fast time may be broken into range bins using an appropriate transformation and mapping (DFT, FFT, etc) with each range bin representing different target distances. Slow time may be the time between pulse transmissions. Thus, a radar receiver may measure the aggregate reflected energy in each range bin over fast time to determine the distance to a target.

The communication device may then receive the plurality of millimeter wave pulses reflected from the environment. The communication device may then sample each of the received millimeter wave pulses 906 at specific time in fast time on each of the receive pulses. The device may then adaptively filter the samples 908. The adaptive filter may remove any mutual coupling component or static object clutter. The communication device may determine if it is the end of sampling in fast time 912. If it is not, the communication device may advance incrementally in fast time 912 and flow will revert to sampling each of the received millimeter wave pulses 906 at specific time in fast time on each of the receive pulses. If it is, the communication device may determine if a human body part is proximate to the device 914. The communication device may then determine if a millimeter wave communication signal may be safely sent 916 from a device such as base station 105 and UE 1100. If the range and the bearing to the human body part make it unsafe to transmit a communication signal the signal will not be sent. If the range and the bearing to the human body part are safe the signal will be sent. Knowledge of the distance and bearing to a human body part may used to determine the directions and power levels for which a communication signal be safely transmitted may be used for selecting a transmit beam, power level or modulation and coding scheme for a communication signal.

Figure 10:
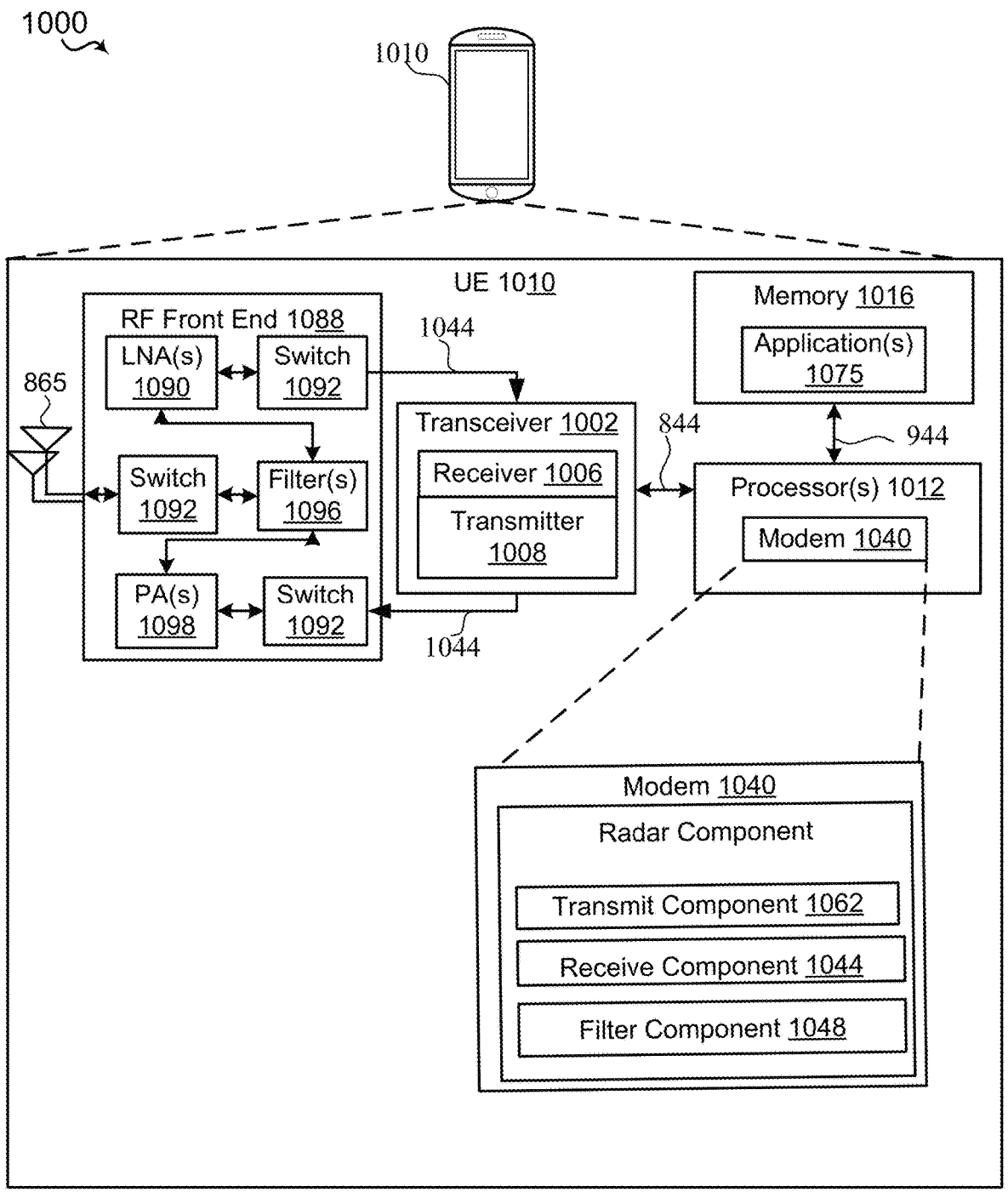
FIG. 10 is an exemplary illustration of a UE in accordance with aspects of the present disclosure.

Referring to FIG. 10, in accordance with various aspects of the present disclosure an example of an implementation of UE 1010 is shown 1000. UE 1010 may be one of the UEs depicted in FIG. 1 for example. It may include a variety of components, some of which have already been described above, but including components such as one or more processors 1012 and memory 1016 and transceiver 1002 in communication via one or more buses 1044, which may operate in conjunction with modem 1040 and the radar component to enable one or more of the functions described herein related to processing a silencing signal or silencing signal request. Further, the one or more processors 1012, modem 1040, memory 1016, transceiver 1002, RF front end 1088 and one or more antennas 1065, may be configured to support voice and/or data calls (simultaneously or non-simultaneously) in one or more radio access technologies as well as radar.

In an aspect, the one or more processors 1012 can include a modem 840 that uses one or more modem processors. The various functions related to a radar component may be included in modem 1040 and/or processors 1012 and, in an aspect, can be executed by a single processor, while in other aspects, different ones of the functions may be executed by a combination of two or more different processors. For example, in an aspect, the one or more processors 1012 may include any one or any combination of a modem processor, or a baseband processor, or a digital signal processor, or a transmit processor, or a receiver processor, or a transceiver processor associated with transceiver 1002. In other aspects, some of the features of the one or more processors 1012 and/or modem 1040 associated with silencing signal component 1050 may be performed by transceiver 1002.

Also, memory 1016 may be configured to store data used herein and/or local versions of applications 1075 or radar component 1050 and/or one or more of its subcomponents being executed by at least one processor 1012. Memory 1016 can include any type of computer-readable medium usable by a computer or at least one processor 1012, such as random-access memory (RAM), read only memory (ROM), tapes, magnetic discs, optical discs, volatile memory, non-volatile memory, and any combination thereof. In an aspect, for example, memory 1016 may be a non-transitory computer-readable storage medium that stores one or more computer-executable codes defining radar component and/or one or more of its subcomponents, and/or data associated therewith, when UE 1010 is operating at least one processor 1012.

Transceiver 1002 may include at least one receiver 1006 and at least one transmitter 1008. Receiver 1006 may include hardware, firmware, and/or software code executable by a processor for receiving data, the code comprising instructions and being stored in a memory (e.g., computer-readable medium). Receiver 1006 may be, for example, a radio frequency (RF) receiver. In an aspect, receiver 1006 may receive signals transmitted by at least one base station. Additionally, receiver 1006 may process such received signals, and also may obtain measurements of the signals, such as, but not limited to, Ec/Io, SNR, RSRP, RSSI, etc. Transmitter 1008 may include hardware, firmware, and/or software code executable by a processor for transmitting data, the code comprising instructions and being stored in a memory (e.g., computer-readable medium). A suitable example of transmitter 808 may including, but is not limited to, an RF transmitter.

Moreover, in an aspect, UE may include RF front end 1088, which may operate in communication with one or more antennas 1065 and transceiver 1002 for receiving and transmitting radio transmissions, for example, wireless communications transmitted by at least one base station or wireless transmissions transmitted by UE. RF front end 1088 may be connected to one or more antennas 1065 and can include one or more low-noise amplifiers (LNAs) 890, one or more switches 1092, one or more power amplifiers (PAs) 1098, and one or more filters 1096 for transmitting and receiving RF signals.

In an aspect, LNA 1090 can amplify a received signal at a desired output level. In an aspect, each LNA 1090 may have a specified minimum and maximum gain values. In an aspect, RF front end 1088 may use one or more switches 1092 to select a particular LNA 1090 and its specified gain value based on a desired gain value for a particular application.

Further, for example, one or more PA(s) 1098 may be used by RF front end 1088 to amplify a signal for an RF output at a desired output power level. In an aspect, each PA 1098 may have specified minimum and maximum gain values. In an aspect, RF front end 1088 may use one or more switches 1092 to select a particular PA 1098 and its specified gain value based on a desired gain value for a particular application.

Also, for example, one or more filters 1096 can be used by RF front end 1088 to filter a received signal to obtain an input RF signal. Similarly, in an aspect, for example, a respective filter 1096 can be used to filter an output from a respective PA 1098 to produce an output signal for transmission. In an aspect, each filter 1096 can be connected to a specific LNA 1090 and/or PA 1098. In an aspect, RF front end 1088 can use one or more switches 1092 to select a transmit or receive path using a specified filter 1096, LNA 1090, and/or PA 1098, based on a configuration as specified by transceiver 1002 and/or processor 1012.

As such, transceiver 1002 may be configured to transmit and receive wireless signals through one or more antennas 1065 via RF front end 1088. In an aspect, transceiver may be tuned to operate at specified frequencies such that UE can communicate with, for example, one or more base stations or one or more cells associated with one or more base stations. In an aspect, for example, modem 1040 can configure transceiver 1002 to operate at a specified frequency and power level based on the UE configuration of the and the communication protocol used by modem 1040.

In an aspect, modem 1040 can be a multiband-multimode modem, which can process digital data and communicate with transceiver 1002 such that the digital data is sent and received using transceiver 1002. In an aspect, modem 1040 can be multiband and be configured to support multiple frequency bands for a specific communications protocol. In an aspect, modem 1040 can be multimode and be configured to support multiple operating networks and communications protocols. In an aspect, modem 1040 can control one or more components of UE (e.g., RF front end 1088, transceiver 1002) to enable transmission and/or reception of signals from the network based on a specified modem configuration. In an aspect, the modem configuration can be based on the mode of the modem and the frequency band in use. In another aspect, the modem configuration can be based on UE configuration information associated with as provided by the network during cell selection and/or cell reselection.

Figure 11:
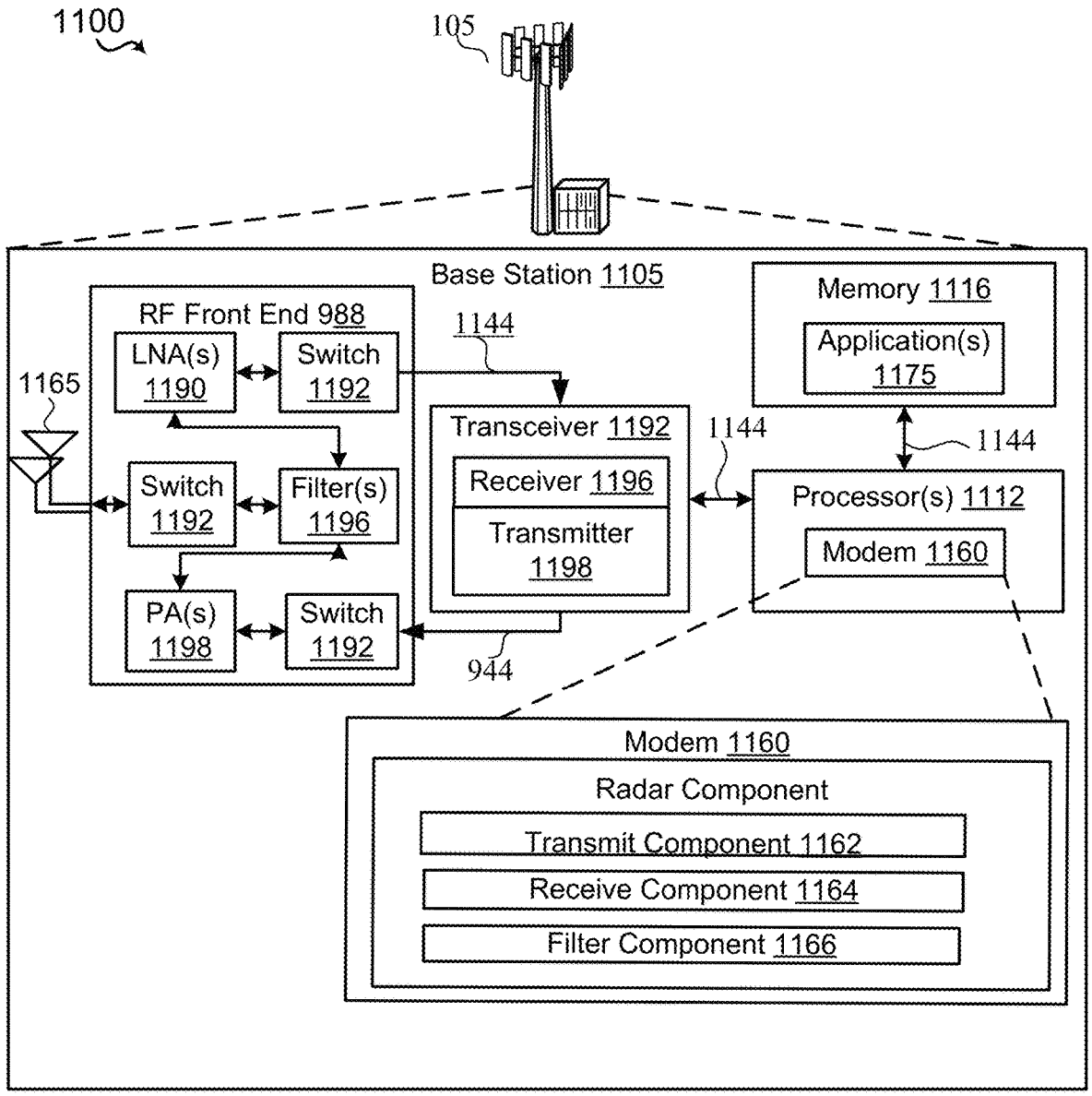
FIG. 11 is an exemplary illustration of a base station in accordance with aspects of the present disclosure.

Referring to FIG. 11, in accordance with various aspects of the present disclosure an example of an implementation of base station, such as one of the base stations 115, that may include a variety of components, some of which have already been described above, but including components such as one or more processors 1112 and memory 1116 and transceiver 1102 in communication via one or more buses 1144, which may operate in conjunction with modem 1160 and fallback component 1170 to enable one or more of the functions described herein related to transmitting an indication channel that indicates whether a current mini-slot includes an URLLC transmission.

The transceiver 1102, receiver 1106, transmitter 1108, one or more processors 1112, memory 1116, applications 1175, buses 1144, RF front end 1188, LNAs 1190, switches 1192, filters 1196, PAs 1198, and one or more antennas 1165 may be the same as or similar to the corresponding components of UE, as described above, but configured or otherwise programmed for base station operations as opposed to UE operations.

It should be noted that the methods described above describe possible implementations, and that the operations and the steps may be rearranged or otherwise modified and that other implementations are possible. Furthermore, aspects from two or more of the methods may be combined.

Techniques described herein may be used for various wireless communications systems such as code division multiple access (CDMA), time division multiple access (TDMA), frequency division multiple access (FDMA), orthogonal frequency division multiple access (OFDMA), single carrier frequency division multiple access (SC-FDMA), and other systems. The terms "system" and "network" are often used interchangeably. A code division multiple access (CDMA) system may implement a radio technology such as CDMA2000, Universal Terrestrial Radio Access (UTRA), etc. CDMA2000 covers IS-2000, IS-95, and IS-856 standards. IS-2000 Releases may be commonly referred to as CDMA2000 1x, 1x, etc. IS-856 (TIA-856) is commonly referred to as CDMA2000 1xEV-DO, High Rate Packet Data (HRPD), etc. UTRA includes Wideband CDMA (WCDMA) and other variants of CDMA. A TDMA system may implement a radio technology such as Global System for Mobile Communications (GSM).

An OFDMA system may implement a radio technology such as Ultra Mobile Broadband (UMB), Evolved UTRA (E-UTRA), Institute of Electrical and Electronics Engineers (IEEE) 802.11 (Wi-Fi), IEEE 802.16 (WiMAX), IEEE 802.20, Flash-OFDM, etc. UTRA and E-UTRA are part of Universal Mobile Telecommunications System (UMTS). LTE and LTE-A are releases of UMTS that use E-UTRA. UTRA, E-UTRA, UMTS, LTE, LTE-A, NR, and GSM are described in documents from the organization named "3rd Generation Partnership Project" (3GPP). CDMA2000 and UMB are described in documents from an organization named "3rd Generation Partnership Project 2" (3GPP2). The techniques described herein may be used for the systems and radio technologies mentioned above as well as other systems and radio technologies. While aspects of an LTE or an NR system may be described for purposes of example, and LTE or NR terminology may be used in much of the description, the techniques described herein are applicable beyond LTE or NR applications.

In LTE/LTE-A networks, including such networks described herein, the term evolved node B (eNB) may be generally used to describe the base stations. The wireless communications system or systems described herein may include a heterogeneous LTE/LTE-A or NR network in which different types of eNBs provide coverage for various geographical regions. For example, each eNB, next generation NodeB (gNB), or base station may provide communication coverage for a macro cell, a small cell, or other types of cell. The term "cell" may be used to describe a base station, a carrier or component carrier associated with a base station, or a coverage area (e.g., sector, etc.) of a carrier or base station, depending on context.

Base stations may include or may be referred to by those skilled in the art as a base transceiver station, a radio base station, an access point, a radio transceiver, a NodeB, eNodeB (eNB), gNB, Home NodeB, a Home eNodeB, or some other suitable terminology. The geographic coverage area for a base station may be divided into sectors making up only a portion of the coverage area. The wireless communications system or systems described herein may include base stations of different types (e.g., macro or small cell base stations). The UEs described herein may be able to communicate with various types of base stations and network equipment including macro eNBs, small cell eNBs, gNBs, relay base stations, and the like. There may be overlapping geographic coverage areas for different technologies.

A macro cell generally covers a relatively large geographic area (e.g., several kilometers in radius) and may allow unrestricted access by UEs with service subscriptions with the network provider. A small cell is a lower-powered base station, as compared with a macro cell, that may operate in the same or different (e.g., licensed, unlicensed, etc.) frequency bands as macro cells. Small cells may include pico cells, femto cells, and micro cells according to various examples. A pico cell, for example, may cover a small geographic area and may allow unrestricted access by UEs with service subscriptions with the network provider. A femto cell may also cover a small geographic area (e.g., a home) and may provide restricted access by UEs having an association with the femto cell (e.g., UEs in a closed subscriber group (CSG), UEs for users in the home, and the like). An eNB for a macro cell may be referred to as a macro eNB. An eNB for a small cell may be referred to as a small cell eNB, a pico eNB, a femto eNB, or a home eNB. An eNB may support one or multiple (e.g., two, three, four, and the like) cells (e.g., component carriers).

The wireless communications system or systems described herein may support synchronous or asynchronous operation. For synchronous operation, the base stations may have similar frame timing, and transmissions from different base stations may be approximately aligned in time. For asynchronous operation, the base stations may have different frame timing, and transmissions from different base stations may not be aligned in time. The techniques described herein may be used for either synchronous or asynchronous operations.

The downlink transmissions described herein may also be called forward link transmissions while the uplink transmissions may also be called reverse link transmissions. Each communication link described herein—including, for example, wireless communications system 100 and 200 of FIGS. 1 and 2—may include one or more carriers, where each carrier may be a signal made up of multiple sub-carriers (e.g., waveform signals of different frequencies).

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

The invention claimed is:

1. A method of detecting a non-static object, the method comprising:
    transmitting a plurality of millimeter wave pulses from a communication device, wherein the plurality of millimeter wave pulses are associated with frequencies within a millimeter wave frequency band;
    receiving reflected energy after transmitting at least one of the plurality of millimeter wave pulses, wherein the reflected energy comprises energy associated with one or more of the plurality of millimeter wave pulses;
    filtering a first signal associated with the reflected energy to obtain a second signal associated with a signal component of the first signal, wherein the signal component represents a static object;
    generating a third signal representative of the non-static object via removal of the second signal associated with the signal component from the first signal associated with the reflected energy; and
    determining whether to transmit a millimeter wave communication signal based at least in part on a range and a direction of the non-static object relative to the communication device, wherein the range and the direction of the non-static object are based at least in part on the third signal representative of the non-static object.

2. The method of claim 1, wherein the non-static object is a human body part.

3. The method of claim 1, wherein
    the signal component represents clutter, antenna mutual coupling, or both, associated with the static object.

4. The method of claim 1, wherein energy reflected from the static object varies slowly relative to energy reflected from the non-static object.

5. The method of claim 4, wherein filtering the reflected energy comprises:
    filtering the first signal associated with the reflected energy by using a sample from a fourth signal associated with previously received reflected energy to extract the energy reflected from the static object which varies slowly relative to the energy reflected from the non-static object, wherein the removal of the second signal is based at least in part on extraction of the energy reflected from the static object.

6. The method of claim 5, wherein filtering the reflected energy comprises:
    filtering the first signal associated with the reflected energy with an adaptive 1-tap cancellation filter, wherein the adaptive 1-tap cancellation filter is based at least in part on the energy reflected from the static object which varies slowly relative to energy reflected from the non-static object.

7. The method of claim 6, wherein filtering the reflected energy comprises:
    filtering the first signal associated with the reflected energy using a single tap delay line.

8. The method of claim 5, wherein filtering the reflected energy comprises:
    filtering the first signal associated with the reflected energy with an infinite impulse response filter or a low pass filter.

9. The method of claim 1, wherein the plurality of millimeter wave pulses are frequency modulated continuous wave pulses.

10. The method of claim 9, wherein each of the plurality of millimeter wave pulses are separated in time by one to one hundred milliseconds.

11. The method of claim 1, wherein a user equipment (UE) is used to transmit the plurality of millimeter wave pulses and receive the reflected energy from the plurality of millimeter wave pulses, or wherein a network entity is used to transmit the plurality of millimeter wave pulses and receive the reflected energy from the plurality of millimeter wave pulses.

12. The method of claim 1, wherein determining whether to transmit the millimeter wave communication signal comprises determining not to transmit the millimeter wave communication signal, determining to make a power adjustment associated with the millimeter wave communication signal, or determining to make a duty cycle adjustment associated with the millimeter wave communication signal.

13. The method of claim 1, wherein the plurality of millimeter wave pulses are continuous wave signals generated by a beating operation of a Phase Modulated Continuous Wave (PMCW) radar processor.

14. An apparatus for detecting a non-static object, the apparatus comprising memory with executable instructions, and one or more processors configured to execute the executable instructions and cause the apparatus to:
    transmit a plurality of millimeter wave pulses, wherein the plurality of millimeter wave pulses are associated with frequencies within a millimeter wave frequency band;
    receive reflected energy after transmitting at least one of the plurality of millimeter wave pulses, wherein the reflected energy comprises energy associated with one or more of the plurality of millimeter wave pulses;
    filter a first signal associated with the reflected energy to obtain a second signal associated with a signal component of the first signal, wherein the signal component represents a static object;

generate a third signal representative of the non-static object via removal of the second signal associated with the signal component from the first signal associated with the reflected energy; and determine whether to transmit a millimeter wave communication signal based at least in part on a range and a direction of the non-static object relative to the apparatus, wherein the range and the direction of the non-static object are based at least in part on the third signal representative of the non-static object.

15. The apparatus of claim 14, wherein the non-static object is a human body part.

16. The apparatus of claim 14, wherein
the signal component represents clutter, antenna mutual coupling, or both, associated with the static object.

17. The apparatus of claim 14, wherein energy reflected from the static object varies slowly relative to energy reflected from the non-static object.

18. The apparatus of claim 17, wherein the one or more processors are configured to execute the executable instructions and cause the apparatus to:
filter the first signal associated with the reflected energy by using a sample from a fourth signal associated with previously reflected energy to extract the energy reflected from the static object which varies slowly relative to the energy reflected from the non-static object, wherein the removal of the second signal is based at least in part on extraction of the energy reflected from the static object.

19. The apparatus of claim 18, wherein the one or more processors are configured to execute the executable instructions and cause the apparatus to:
filter the first signal associated with the reflected energy with an infinite impulse response filter or a low pass filter.

20. The apparatus of claim 19, wherein the one or more processors are configured to execute the executable instructions and cause the apparatus to:
filter the first signal associated with the reflected energy using a single tap delay line.

21. The apparatus of claim 14, wherein the plurality of millimeter wave pulses are frequency modulated continuous wave pulses.

22. The apparatus of claim 21, wherein each of the plurality of millimeter wave pulses are separated in time by one to one hundred milliseconds.

23. The apparatus of claim 14, wherein the apparatus is a user equipment (UE) or a base station.

24. The apparatus of claim 23, wherein the non-static object is a human body part.

25. The apparatus of claim 14, wherein to determine whether to transmit the millimeter wave communication signal, the one or more processors are configured to execute the executable instructions and cause the apparatus to determine not to transmit the millimeter wave communication signal, determine to make a power adjustment associated with the millimeter wave communication signal, or determine to make a duty cycle adjustment associated with the millimeter wave communication signal.

26. The apparatus of claim 25, wherein
the signal component represents clutter, antenna mutual coupling, or both, associated with the static object.

27. The apparatus of claim 14, wherein the plurality of millimeter wave pulses are continuous wave signals generated by a beating operation of a Phase Modulated Continuous Wave (PMCW) radar processor.

28. The apparatus of claim 27, wherein energy reflected from the static object varies slowly relative to energy reflected from the non-static object.

29. An apparatus for detecting a non-static object, the apparatus comprising:
means for transmitting a plurality of millimeter wave pulses, wherein the plurality of millimeter wave pulses are associated with frequencies within a millimeter wave frequency band;
means for receiving reflected energy after transmitting at least one of the plurality of millimeter wave pulses, wherein the reflected energy comprises energy associated with one or more of the plurality of millimeter wave pulses;
means for filtering a first signal associated with the reflected energy to obtain a second signal associated with a signal component of the first signal, wherein the signal component represents a static object;
means for generating a third signal representative of the non-static object via removal of the second signal associated with the signal component from the first signal associated with the reflected energy; and
means for determining whether to transmit a millimeter wave communication signal based at least in part on a range and a direction of the non-static object relative to the apparatus, wherein the range and the direction of the non-static object are based at least in part on the third signal representative of the non-static object.

30. A non-transitory computer-readable medium storing computer executable code, the code executable to:
transmit a plurality of millimeter wave pulses, wherein the plurality of millimeter wave pulses are associated with frequencies within a millimeter wave frequency band;
receive reflected energy after transmitting at least one of the plurality of millimeter wave pulses, wherein the reflected energy comprises energy associated with one or more of the plurality of millimeter wave pulses;
filter a first signal associated with the reflected energy to obtain a second signal associated with a signal component of the first signal, wherein the signal component represents a static object;
generate a third signal representative of a non-static object via removal of the second signal associated with the signal component from the first signal associated with the reflected energy; and
determine whether to transmit a millimeter wave communication signal based at least in part on a range and a direction of the non-static object relative to a communication device comprising the non-transitory computer-readable medium, wherein the range and the direction of the non-static object are based at least in part on the third signal representative of the non-static object.

* * * * *